(12) United States Patent
Barry

(10) Patent No.: US 12,708,688 B2
(45) Date of Patent: Aug. 18, 2026

(54) STETHOSCOPE SANITIZER

(71) Applicant: Gates Barry, Macon, GA (US)

(72) Inventor: Gates Barry, Macon, GA (US)

( * ) Notice: Subject to any disclaimer, the term of this patent is extended or adjusted under 35 U.S.C. 154(b) by 1038 days.

(21) Appl. No.: 17/843,877

(22) Filed: Jun. 17, 2022

(65) Prior Publication Data

US 2023/0016446 A1 Jan. 19, 2023

Related U.S. Application Data

(60) Provisional application No. 63/211,878, filed on Jun. 17, 2021.

(51) Int. Cl.

| | |
|---|---|
| ***A61L 2/00*** | (2006.01) |
| ***A61L 2/18*** | (2006.01) |
| ***A61L 2/26*** | (2006.01) |
| ***B65D 83/10*** | (2006.01) |
| *A61L 103/15* | (2026.01) |

(52) U.S. Cl.

CPC .................. *A61L 2/26* (2013.01); *A61L 2/18* (2013.01); *A61L 2103/15* (2026.01); *A61L 2202/15* (2013.01)

(58) Field of Classification Search

CPC .......... A61B 19/02; A61B 7/02; B65D 81/10; A61M 5/10; A47L 1/02; A61L 2/00; A61L 2/18; A61L 2202/00

USPC ...... 422/5, 28, 292, 300; 206/363–364, 370; 181/131; 15/97.1; 128/213

See application file for complete search history.

(56) References Cited

U.S. PATENT DOCUMENTS 4,568,521 A * 2/1986 Spector .................. A61L 9/122 136/246
5,041,264 A * 8/1991 Williams ............... A61B 50/36 383/110
2012/0051969 A1* 3/2012 Nahman .................. A61B 7/02 422/28

* cited by examiner

*Primary Examiner* — Monzer R Chorbaji
(74) *Attorney, Agent, or Firm* — Trace H. Jackson; Rogers Towers, P.A.

(57) ABSTRACT

An improved stethoscope sanitization device. A wall-mounted cabinet having a removable sanitization pad within may be opened to expose a stethoscope to the sanitization pad. By rubbing the stethoscope over the sanitization pad, the stethoscope may be sterilized by applying it to the sanitization pad. Additionally, a release mechanism on the base of the sanitization device may be actuated to allow for replacement of the sanitization pad.

4 Claims, 2 Drawing Sheets

STETHOSCOPE SANITIZER

FIELD OF THE INVENTION

This application claims the benefit of the priority of U.S. Provisional Patent Application No. 63/211,878, filed on Jun. 17, 2021, and entitled Stethoscope Sanitizer.

FIELD OF THE INVENTION

The present invention relates to a method and apparatus for improved sanitization of stethoscopes and ultrasound/doppler probes.

BACKGROUND OF THE INVENTION

The SARS-CoV-2 pandemic has caused a renewed appreciation for personal protective equipment. This includes finding new ways to sanitize objects that touch or otherwise interface with multiple people.

Presently, one such object that is not frequently sanitized is a physician's stethoscope. Stethoscopes are acoustic medical devices for listening to the internal sounds of a body. They typically include a drum (also known as a resonator) that is placed against the skin of the body and includes one or two tubes connected to two earpieces. However, there is presently no efficient way to sanitize the drum between patient visits. The same can be said of both doppler devices and ultrasound probes. Doppler devices listen for pulses in extremities to ensure proper blood flow and to assess fetal heart tones. Ultrasound machines are used for a wide variety of reasons and are utilized in nearly every field of medicine. Both devices have a probe-like end that comes into contact with each patient that it is used on.

Inconsistent stethoscope/ultrasound probe sanitization practices can lead to hospital-acquired, nosocomial infections. These infections, by their nature, can be more difficult to treat than other infections. Thus, there is a strong interest in better stethoscope and doppler/ultrasound probe sanitization practices.

Current strategies for cleaning stethoscopes are nearly as old as the stethoscopes themselves. Wipes of various chemical compounds are used. Some of these chemicals will eventually cause the breakdown of various materials used in the stethoscope's construction, ultimately necessitating their replacement. These precise tools can cost up to $600 depending on the model. Still other cleaning chemicals are harsh to the skin and require the individual cleaning to don gloves during the cleaning process, utilizing both time and resources. Because the current process is not centralized and is time-consuming, healthcare workers are less likely to clean their stethoscopes which increases the risk of spreading infection through these fomites that come in contact with every patient they see. The same can be said for cleaning of probes which are currently cleaned using the same techniques used to clean stethoscopes.

SUMMARY OF THE INVENTION

Accordingly, the present invention provides an apparatus for improved sanitization of stethoscopes. A wall-mounted stethoscope/probe sanitizer includes a base unit with a sanitizing substance on a removable sanitizing pad. The sanitizer may include a release mechanism to allow for the swapping out of the pad. In some embodiments, the sanitizer may include an opening flap to preserve the viscosity of the sanitizing substance. The flap may open using a spring or a hinge. Other variations may be without a flap altogether and instead utilize a semi-permeable membrane to clean the surface of the stethoscope/probe while preventing the solution from evaporating. Base units may also be mounted on the ultrasound machines themselves or other convenient locations.

DESCRIPTION OF THE DRAWINGS

The accompanying drawings, which are incorporated in and constituted a part of this specification, illustrate several embodiments of the disclosure. Together with the description, these drawings serve to explain the principles of the disclosure.

DETAILED DESCRIPTION

The present invention relates to an improved stethoscope/probe sanitizer.

In the following sections, detailed descriptions of examples and methods of the invention will be given. The description of both preferred and alternative examples, though thorough, are exemplary only. It is understood that, to those skilled in the art, various, modifications, and alterations may be apparent. The examples do not limit the broadness of the aspects of the underlying invention as defined by the claims.

Figure 1:
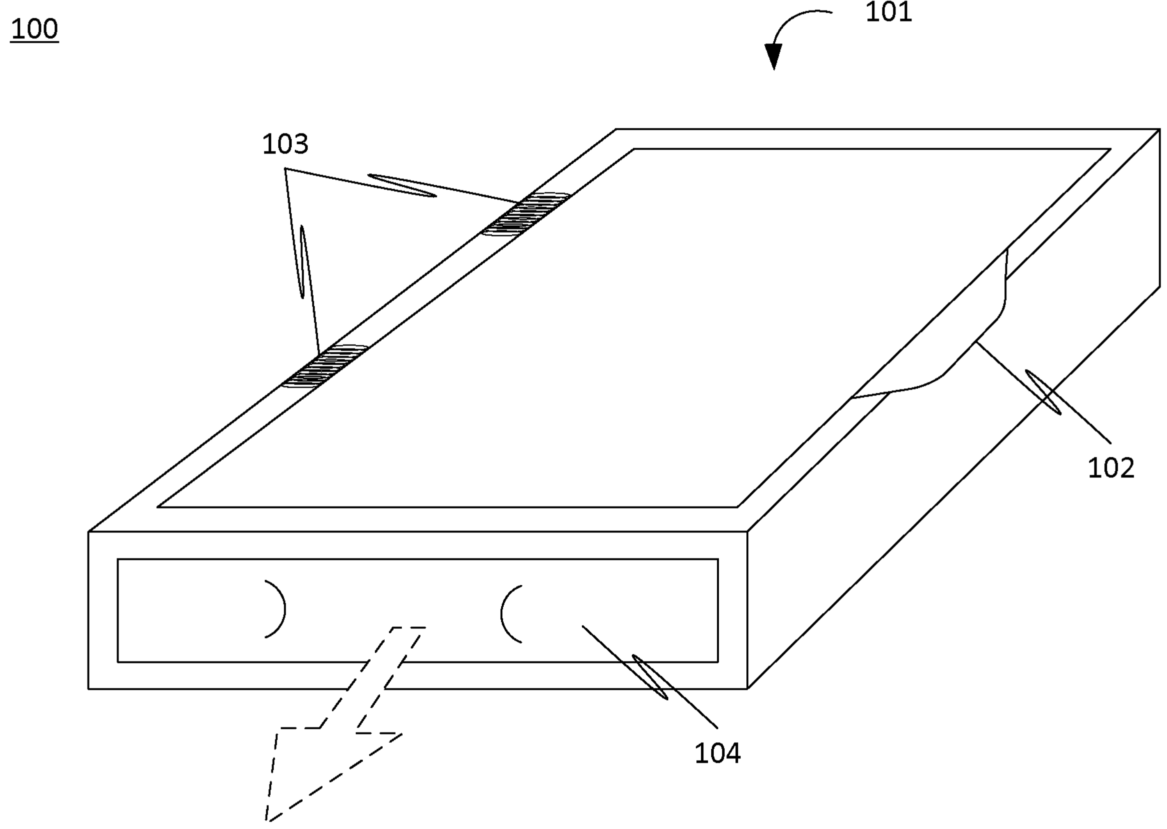
FIG. 1 illustrates an exemplary embodiment of a wall-mounted stethoscope/probe sanitizer.

Referring now to FIG. 1, an exemplary embodiment of a wall-mounted stethoscope sanitizer 100 is shown in a closed state. The mounted stethoscope sanitizer may comprise base 101, opening flap 102, hinge 103, and release mechanism 104. Base 101 may have an opening flap 102 attached to the base 101 by hinge 103. Hinge 103 may be a spring, a springe hinge, a standard hinge, or any other mechanism allowing for a simple opening of the opening flap 102. In some embodiments, opening flap 102 may further include an extruding tab to allow for easier opening. It may also include such a mechanism to work in combination with hinge 103 for the use of more simple operation.

The base 101 may be, for example, a substantially hollow box, covered by opening flap 102. This box may have sufficient interior dimension to allow the placement of a disposable, internal sanitizing pad. The sanitizing pad may be attached to the interior of the box with a suitably strong adhesive. This adhesive may include, for example, a 3M strip or clue. In some embodiments, as discussed below, the internal sanitizing pad may be a replaceable, integral component of the base.

Base 101 may further include, on an end of base 101, a release mechanism 104 to easily allow an internal sanitizing pad to be replaced. Release mechanism 104 may be spring-loaded, Velcro, use snaps, use clips, or be any other means of removably locking in place the internal sanitizing pad. The release mechanism may be an integral component of base 101 or it may be a removable base that may come partially or completely detached from base 101 when the internal sanitizing pad is removed. In some embodiments, release mechanism 104 may further include a drain to allow for drainage of any excess liquid from the internal sanitization pad.

One surface of base 101 may include an adhesive. In exemplary embodiments, this will be a rear surface of base 101 relative to the surface of base 101 including opening flap 102. The adhesive may be permanently affixed to base 101 or may be removably affixed to base 101. The adhesive may include a 3M double-sided adhesive. It may also include various hooks, slots, and other means of attachment to surfaces including but not limited to walls, sinks, hospital beds, and other pieces of medical equipment.

Figure 2:
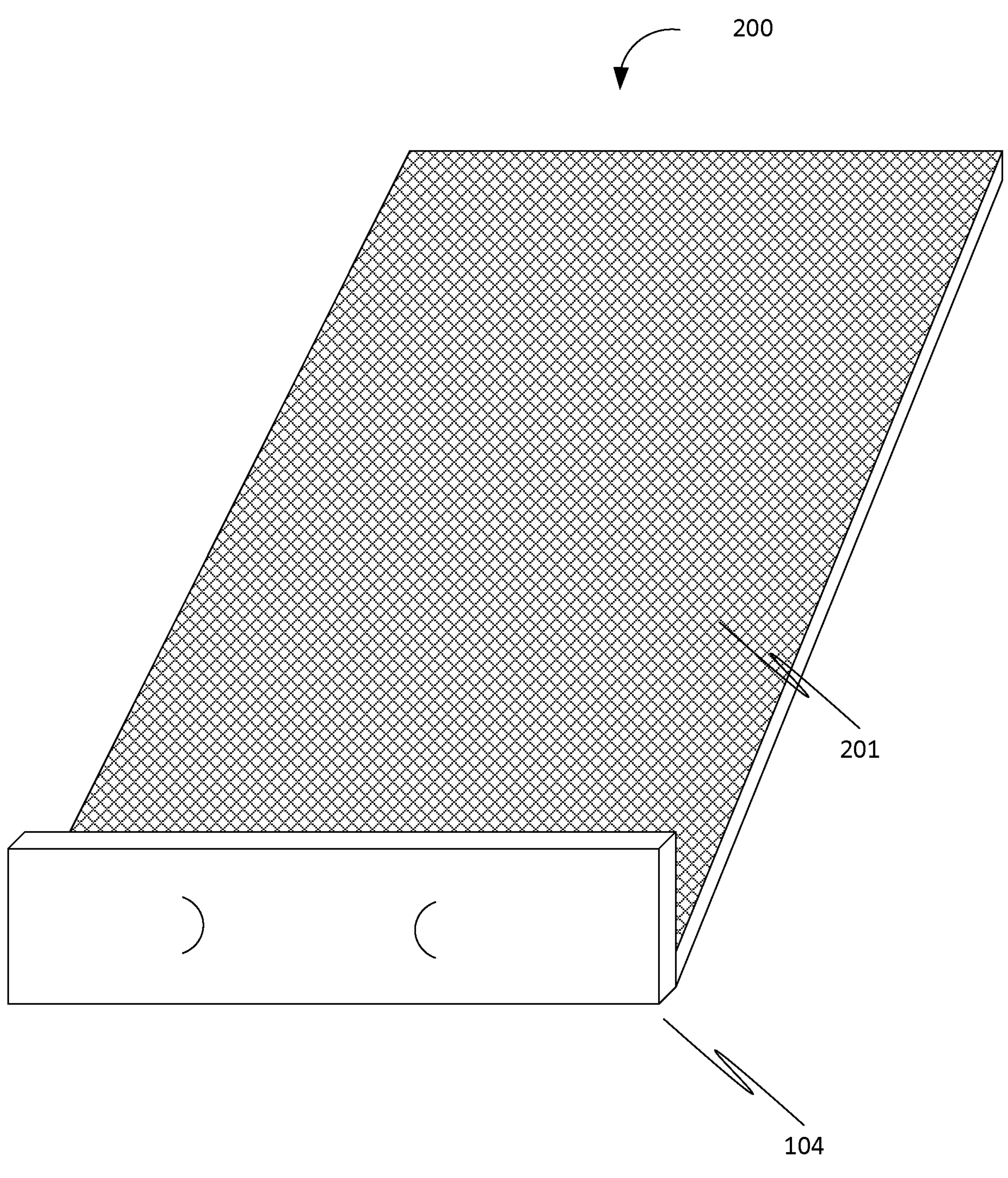
FIG. 2 illustrates an exemplary sanitizing pad.

Referring now to FIG. 2, an exemplary embodiment of internal sanitizing pad 200 is shown. In this embodiment, internal sanitizing pad 200 is shown together with release mechanism 104 in an embodiment of the invention in which the release mechanism 104 comes detached from base 101 when replacing the sanitizing pad. Internal sanitizing pad 200 includes a disposable sanitary pad 201. Disposable sanitary pad may be removably attached to internal sanitizing pad 200, such as by Velcro or other removable adhesive, or it may simply fit snugly on internal sanitizing pad 200 when the latter is placed within base 101. In some embodiments, the sanitizing pad may be coated or work in junction with a semipermeable membrane that allows unidirectional flow of cleaning solution and may possibly eliminate the need for a closing lid. This exemplary membrane may be constructed of cellulose, cellulose containing compounds, and other materials.

Disposable sanitary pad 201 may be partially or fully saturated with a sanitization liquid. The sanitization liquid may include a solution of isopropyl alcohol (in exemplary embodiments, this solution will have a concentration of 70% isopropyl alcohol, but the precise concentration may be determined according to the given need and may be any concentration in the range of 0.001%-100%), water, ethanol alcohol, alkyl, hydrogen peroxide, vinegar, distilled spirits, or various chloride compounds, or any combination thereof. In some embodiments, the sanitization pad will be sufficiently saturated to require replacement only after one week.

Using the opening flap, the base can be opened to expose disposable sanitary pad 201. A stethoscope, ultrasound probe, or other medical device can then be rubbed on, applied against, or in some other way put into contact with the disposable sanitary pad 201. By then closing the opening flap, the sanitary pad 201 may be exposed to less ambient air, which may slow the drying out of the sanitary pad 201 (i.e., the evaporation of the cleansing, sanitizing liquid in which sanitary pad 201 is saturated). When it is necessary to replace the sanitary pad 201, the release mechanism can be actuated to release the sanitary pad 201, the sanitary pad 201 can be replaced with a second sanitary pad 201, and the sanitary pad 201 and release mechanism can be replaced within the base.

CONCLUSION

Several embodiments of the present disclosure have been described. While this specification contains many specific implementation details, these should not be construed as limitations on the scope of any disclosures or of what may be claimed, but rather as descriptions of features specific to particular embodiments of the present disclosure. While embodiments of the present disclosure are described herein by way of example using several illustrative drawings, those skilled in the art will recognize the present disclosure is not limited to the embodiments or drawings described. It should be understood the drawings and the detailed description herein are not intended to limit the present disclosure to the form disclosed. Instead, the present disclosure is meant to encompass modifications, equivalents, and alternatives falling within the spirit and scope of embodiments of the present disclosure, as defined by the appended claims.

The headings used herein are for organization purposes only and are not meant to be used to limit the scope of the description or the claims. As used throughout this application, the word “may” is used in a permissive sense (i.e., meaning having the potential to), rather than the mandatory sense (i.e., meaning must). Similarly, the word “include” (and derivatives thereof) means including but not limited to. To facilitate understanding, like reference numerals have been used, where possible, to designate like elements common to the figures.

The phrases “at least one,” “one or more,” and “and/or” are open-ended expressions that are both conjunctive and disjunctive in operation. For example, each of the expressions “at least one of A, B, and C,” “at least one of A, B, or C,” “one or more of A, B, and C,” “one or more of A, B, or C,” and “A, B, and/or C” means A alone, B alone, C alone, A and B together, A and C together, B and C together, or A, B, and C together.

The term “a” or “an” entity means one or more of that entity. As such, “a”/“an,” “one or more,” and “at least one” are used interchangeably herein. Additionally, “comprising,” “including,” and “having” can be used interchangeably.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination an, in some cases, be excised from the combination, and the claimed combination may be directed to a sub-combination or a variation of a sub-combination.

What is claimed is:

1. A stethoscope sanitizer comprising:

a base having an opening flap actuated by a hinge and comprising a substantially hollow interior;

a sanitizing pad in the interior; and a release mechanism on one end of the base in contact with the sanitizing pad, wherein the release mechanism comprises clips that attach to the interior of the base.

2. The stethoscope sanitizer of claim 1, wherein a surface of the base comprises an adhesive for affixing to a surface of a medical environment.

3. The stethoscope sanitizer of claim 1, wherein the sanitizing pad is saturated in a solution of isopropyl alcohol.

4. The stethoscope sanitizer of claim 1, wherein the sanitizing pad is saturated in a solution of ethanol alcohol.

* * * * *